United States Patent [19]
Chevalier et al.

[11] Patent Number: 6,063,389
[45] Date of Patent: May 16, 2000

[54] COMPOSITION FOR DEPIGMENTING OR BLEACHING MAMMALIAN SKIN CONTAINING L-2-OXOTHIAZOLIDINE-4-CARBOXYLIC ACID AND A POLYOL

[75] Inventors: Véronique Chevalier, Villecresnes; Jean-Baptiste Galey, Aulnay Sous Bois, both of France

[73] Assignee: L'Oreal, Paris, France

[21] Appl. No.: 09/022,052

[22] Filed: Feb. 11, 1998

Related U.S. Application Data

[63] Continuation-in-part of application No. 08/773,514, Dec. 23, 1996.

[30] Foreign Application Priority Data

Dec. 22, 1995 [FR] France .................................. 95 15335

[51] Int. Cl.$^7$ .................................................. A61K 7/135
[52] U.S. Cl. ......................... 424/401; 424/62; 514/937; 514/846
[58] Field of Search ....................... 424/62, 401; 426/72; 514/846, 937

[56] References Cited

U.S. PATENT DOCUMENTS

Re. 34,185  2/1993  Amick ...................................... 548/213

FOREIGN PATENT DOCUMENTS 0 656 201  6/1995  European Pat. Off. .
0 780 120  6/1997  European Pat. Off. .

*Primary Examiner*—Thurman K. Page
*Assistant Examiner*—Sharon Howard
*Attorney, Agent, or Firm*—Oblon, Spivak, McClelland, Maier & Neustadt, P.C.

[57] ABSTRACT

A cosmetic composition for depigmenting or bleaching mammalian skin or both, which contains:

a) an amount of L-2-oxothiazolidine-4-carboxylic acid effective to depigment or bleach mammalian skin or both, and b) one or more polyols, c) a topically-acceptable carrier.

23 Claims, No Drawings

COMPOSITION FOR DEPIGMENTING OR BLEACHING MAMMALIAN SKIN CONTAINING L-2-OXOTHIAZOLIDINE-4-CARBOXYLIC ACID AND A POLYOL

The present application is a continuation-in-part (CIP) Application of application Ser. No. 08/773,514, filed on Dec. 23, 1996.

BACKGROUND OF THE INVENTION

1. Field of the Invention

The present invention relates to a composition for depigmenting or bleaching mammalian skin containing L-2-oxothiazolidine-4-carboxylic acid and at least one polyol.

2. Discussion of the Background

The color of mammalian skin, such as human, depends on many factors and, in particular, on the seasons of the year, race and sex, for example. It is, however, mainly determined by the concentration of melanin produced by melanocytes.

For several years attempts have been made to reduce and/or slow down production of melanin in order to depigment or bleach the skin, by acting on one or more of the intermediates produced in the intracellular biochemical synthesis of melanin. In this effort, different chemical entities have been tested and used as depigmenting or bleaching agents. In particular, compounds such as vitamin C, vitamin C derivatives or vitamin E derivatives, arbutin, hydroquinone, kojic acid, placenta derivatives and glutathione and derivatives thereof have been incorporated into compositions and tested.

The above compounds are known to act on the synthesis and/or activity of tyrosinase, an enzyme which plays a part in the synthesis of melanin, or are known to reduce the amount of melanin formed or, alternatively, are known to stimulate the removal of melanin via keratinocytes. Unfortunately, these compounds are either toxic when applied to the skin, in the case of hydroquinone, are unstable in solution, in the case of vitamin C and kojic acid, which complicates the manufacture of the composition, or have unpleasant odors, in particular, sulphurous odors, such as glutathione, which consequently limits the use thereof. Moreover, the above tyrosinase- or tyrosinase synthesis-inhibitors are very limited in number.

It is also known to use L-2-oxothiazolidine-4-carboxylic acid in cosmetic or dermatological compositions intended for topical application for prevention of hair loss or to stimulate the regrowth of hair, as described in EP-656,201.

However, procysteine has a certain level of instability, in particular when it is in the presence of water. Thus, when it is introduced into a cosmetic composition, in particular a composition containing water, its efficiency decreases over time. In addition, the composition into which it is introduced shows signs of degradation, i.e., coloration and odor, after a certain period of storage, which are, of course, unacceptable to users.

Thus, a need exists for a skin bleaching agent which is as effective in its action as those that are known but which avoids the above drawbacks, i.e., one which is stable in a composition, which is not toxic to the skin and which has no unpleasant odors, particularly upon application.

A need also exists for a composition which can be used in cosmetic and/or dermatological fields containing L-2-oxothiazolidine-4-carboxylic acid, the latter remaining stable over time.

SUMMARY OF THE INVENTION

Accordingly, it is one object of the present invention to provide a skin depigmenting or bleaching agent which is non-toxic and has no unpleasant odors.

It is, moreover, an object of the present invention to provide a method for depigmenting or bleaching skin.

It is further an object of the present invention to provide a composition containing L-2-oxothiazolidine4-carboxylic acid (I) and a polyol (II), which is unexpectedly stable, particularly in media containing water.

The above objects and others are provided by a composition which contains L-2-oxothiazolidine-4-carboxylic acid and a polyol, and a topically acceptable carrier, which is suitable for cosmetic and/or dermatological applications.

DETAILED DESCRIPTION OF THE PREFERRED EMBODIMENTS

The present invention is predicated, in part, upon the surprising discovery that L-2-oxothiazolidine-4-carboxylic acid may be used, quite effectively, to depigment or bleach mammalian skin. This is, indeed, surprising since, conventionally, L-2-oxothiazolidine4-carboxylic acid has only been used as a hair loss inhibitor as in EP 0 656 201 A1.

The present invention is also predicated, in part, upon the surprising discovery that the combination of L-2-oxothiazolidine-4-carboxylic acid or procysteine, denoted as compound (I) and at least one polyol, denoted as compound (II), affords a marked enhancement in the stability of compound (I), particularly in media containing water.

The present invention, thus, provides a composition containing L-2-oxothiazolidine-4-carboxylic acid and at lease one polyol in a cosmetic or dermatological composition as a depigmenting and/or bleaching agent.

The present invention also provides a method for the preparation of a dermatological composition for depigmenting an/or bleaching of mammalian, particularly human, skin.

On the contact with skin, L-2-oxothiazolidine-4-carboxylic acid affords the surprising advantage of not generating an unpleasant release of sulphurous odor.

In accordance with a first aspect of the present invention, L-2-oxothiazolidine-4-carboxylic acid may be present in the present composition in an amount ranging from about 0.1 to 10% by weight and preferably from about 2 to 5% by weight relative to the total weight of the composition. Moreover, the amount of the composition applied on the skin may vary and depends upon the user. Thus, for example, if 10 g of composition were applied, from about 0.01 to 1 g of L-2-oxothiazolidine-4-carboxylic acid would be administered. However, amounts of more or less than this amount may be used as desired. Generally, the more compound used, the greater the bleaching effect obtained.

The composition according to the present invention may further contain any one or more ingredients conventionally used in the cosmetic or dermatological field, in standard or conventional concentrations. These ingredients may, for example, be fatty substances, preserving agents, vitamins, gelling agents, fragrances, surfactants, water, antioxidants, fillers, moisturizers or screening agents, or mixtures thereof.

Among the fatty substances which may be used are a mineral or synthetic oil, a wax, a silicone, a fatty alcohol or a fatty acid. The oil may be liquid petrolatum or jojoba oil, and the wax may be sipol wax, for example. These oils and these waxes may be of either natural or synthetic origin.

The surfactants may be sodium mono diglyceryl stearate or sodium stearate, for example, and the gelling agents may be polyethylene glycols, which are optionally oxyethylenated.

The composition of the present invention may be in the form of an aqueous, aqueous-alcoholic or oily solution, an oil-in-water or water-in-oil emulsion, an aqueous or oily gel, or a dispersion of vesicles, in particular lipid vesicles, for example. This composition may be relatively fluid and have the appearance of a cream, an ointment, a milk, a lotion, a paste or a foam, for example. This composition may optionally be applied to the skin in aerosol form.

The present invention also relates to a cosmetic and/or dermatological process for depigmenting and/or bleaching mammalian skin, which entails applying to the skin of a mammal in need thereof an effective amount of L-2-oxothiazolidine-4-carboxylic acid, preferably in a composition containing the same.

The first aspect of the present invention will now be further illustrated by several examples which follow, in which concentrations are given as percentage by weight. These examples are provided solely for purposes of illustration and are not intended to be limitative.

EXAMPLE 1
Bleaching cream for the face

| | |
|---|---|
| L-2-Oxothiazolidine-4-carboxylic acid | 2 |
| Sodium stearate | 3 |
| Liquid petrolatum | 6 |
| Alkyl paraben | 0.05 |
| Potassium sorbate | 10 |
| Stearyl alcohol | 1 |
| Fragrance | 1 |
| Water | 100 |

EXAMPLE 2
Bleaching cream for the body

| | |
|---|---|
| L-2-Oxothiazolidine-4-carboxylic acid | 5 |
| Jojoba oil | 13 |
| Sipol wax | 6 |
| Isopropyl palmitate | 2 |
| Glycerol | 15 |
| Alkyl paraben | 0.5 |
| Fragrance | 1 |
| Water | 100 |

The second aspect of the present invention affords a composition containing L-2-oxothiazolidine-4-carboxylic acid or procysteine, denoted as compound (I), with at least one polyol, denoted as compound (II), the amounts by weight of compounds (I) and (II) being respectively denoted as [I] and [II] and following the relationship [I]/[II]≦1/3.

Peferably, the ratio [I]/[II]≦1/4 and even more preferably the ratio [I]/[II]≦1/5.

This aspect of the present invention also affords a cosmetic composition containing the above combination and water. This composition contains a cosmetically acceptable carrier or support, of which water is one of the constituents. The elements of the carrier or support are chosen, in particular, such that the composition is non-irritating, non-toxic and non-allergenic.

Preferably, the present composition contains:
L-2-oxothiazolidine-4-carboxylic acid (I)
at least one polyol (II)
water
the amounts by weight of the components (I) and (II) being respectively denoted as [I] and [II] and following the relationship: [I]/[II]≦1/3,
the amount of water being less than or equal to 35% by weight relative to the total weight of the composition, preferably less than or equal to 30%, even more preferably less than or equal to 20%.

Such compositions make it possible to transport procysteine stably over time without any loss of this active agent's efficacy.

The term "polyol" includes, for example, linear, branched or cyclic, saturated or unsaturated alkyl polyols bearing at least two —OH functions on the alkyl chain, as well as the polymers (polyethers) of these polyhydroxylated alkyl compounds. Preferably, it is an alkyl compound having from 2 to about 12 carbon atoms, and even more preferably from 2 to about 8 carbon atoms. Advantageously, this alkyl compound contains 2 or 3 carbon atoms.

The polyol used according to the invention can be chosen in particular from glycerol, ethylene glycol, propylene glycol, polymers and copolymers of glycerol, of ethylene glycol and of propylene glycol, such as, for example, dipropylene glycol and hexaglycerol.

Among the polyols which can be used according to the invention, mention may also be made of sorbitol, hexylene glycol, butylene glycol, pentylene glycol, butyldiglycol and 1,2,3-trihydroxyhexane, for example.

The composition as described above, may be advantageously used for the depigmentation or bleaching of human skin or of human head hair or other hair. However, the composition may also be used to prevent hair loss or to stimulate the regrowth of hair.

Advantageously, the composition according to the invention contains from about 0.1 to 10% by weight of L-2-oxothiazolidine-4-carboxylic acid preferably from about 0.1 to 5%, even more preferably from about 0.5 to 3%, by weight relative to the total weight of the composition.

The present composition may be in any pharmaceutical form usually used for topical application, in particular in the form of an aqueous, aqueous-alcoholic or oily solution, an oil-in-water or water-in-oil emulsion or a multiple emulsion, an aqueous or oily gel, a solid, pasty or liquid anhydrous product, a dispersion of oil in an aqueous phase using spherules, it being possible for these spherules to be polymer nanoparticles such as nanospheres and nanocapsules or lipid vesicles of ionic and/or nonionic type.

This composition can be more or less fluid and have the appearance of a white or colored cream, an ointment, a milk, a lotion, a serum, a paste or a mousse. It can optionally be applied to the skin or to the hair in aerosol form. It can also be in solid form and, for example, in stick form. It can be used as a care product and/or as a make-up product. It can also be in the form of a shampoo or conditioner.

In a known manner, the composition of the invention can also contain the usual adjuvants in the cosmetic and dermatological fields, such as hydrophilic or lipophilic gelling agents, hydrophilic or lipophilic active agents, preserving agents, antioxidants, solvents, fragrances, fillers, screening agents, pigments, odor absorbers and dyestuffs. The amounts of these various adjuvants are those used conventionally in the fields considered and, for example, from 0.1 to 20% of the total weight of the composition. Depending on their nature, these adjuvants can be introduced into the fatty phase, into the aqueous phase, into the lipid vesicles and/or into the nanoparticles.

When the composition of the invention is an emulsion, the proportion of the fatty phase can range from 5 to 80% by weight, and preferably from 5 to 50% by weight, relative to the total weight of the composition. The oils, the emulsifiers and the co-emulsifiers used in the composition in emulsion form are chosen from those used conventionally in the field considered. The emulsifier and the co-emulsifier are present in the composition in a proportion ranging from 0.3 to 30% by weight, and preferably from 0.5 to 20% by weight, relative to the total weight of the composition.

As oils which can be used in the invention, mention may be made of mineral oils (liquid petroleum jelly), oils of the plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnuba wax, ozokerite) can also be used as fatty substances.

As emulsifiers and co-emulsifiers which can be used in the invention, mention may be made, for example, of fatty acid esters of polyethylene glycol, such as PEG-20 stearate, and fatty acid esters of glycerol, such as glycerol stearate.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and, as lipophilic agents, mention may be made of modified clays such as bentenes, metal salts of fatty acids, hydrophobic silica and polyethyenes.

Vitamins, ketatolytic agents and/or desquamating agents (salicylic acid and its derivatives, α-hydroxy acids, ascorbic acid and its derivatives), anti-inflammatory agents, calmants and mixtures thereof can be used in particular as active agents. The combination according to the invention can also be combined with other depigmenting agents, such as cojic acid or hydroquinone and its derivatives, which makes it possible to use the latter agents at doses that are less toxic to the skin. The combination according to the invention can also be combined with other anti-hair-loss and/or hair-regrowth agents. In case of incompatibility, these active agents and/or the combination according to the invention can be incorporated into spherules, in particular ionic or nonionic vesicles and/or nanoparticles (nanocapsules and/or nanospheres) so as to isolate them from each other in the composition.

Advantageously, the aqueous phase of the composition is neutralized by adjusting its pH to a value between about 6 and 8.

The examples which follow are given by way of illustration of the invention and are not intended to be limitative. The percentages are given by weight relative to the total weight of each constituent of the composition.

EXAMPLE 3

Facial depigmenting cream

| Procystein | 1% |
|---|---|
| Apricot oil | 3% |
| Triethanolamine | 1% |
| Aluminum starch octenyl succinate | 3% |
| Nylon powder | 7% |
| Cyclomethicone and dimethone copolyol | 20% |
| Phenyltrimethicone | 4% |
| Propylene glycol | 6% |
| Glycerol | 23% |
| EDTA | q.s. |
| Preserving agents | q.s. |
| Water | 31.5% |

EXAMPLE 4

Facial depigmenting cream

| Procysteine | 1% |
|---|---|
| Apricol oil | 3% |
| Fillers | 10% |
| Cyclomethicone | 12.5% |
| Cyclomethicone and dimethicon copolyol | 20% |
| Phenyltrimethicone | 4% |
| Propylene glycol | 6% |
| Glycerol | 23% |
| EDTA | q.s. |
| Preserving agents | q.s. |
| Water | 19% |

Having described the present invention, it will be apparent to the artisan that many changes and modifications may be made to the above-described embodiments without departing from the spirit and the scope of the present invention.

What is claimed as new and desired to be secured by Letters Patent of the United States is:

1. A topical composition, comprising at least L-2-oxothiazolidine-4-carboxylic acid (I), and at least one polyol (II), the amounts by weight of compounds (I) and (II) being in the relationship: $(I)/(II) \leq 1/3$.

2. The topical composition of claim 1, wherein said L-2-oxothiazolidine-4-carboxylic acid is present in an amount of from about 0.1 to 10% by weight based upon the total weight of the composition.

3. The topical composition of claim 2, wherein said L-2-oxothiazolidine-4-carboxylic acid is present in an amount of from about 2 to 5% by weight.

4. The topical composition of claim 1, which is in a form of an aqueous solution, aqueous-alcoholic solution, oily solution, oil-in-water emulsion, water-in-oil solution, aqueous gel, oily gel or vesicle dispersion.

5. The topical composition of claim 1, which further comprises one or more of fatty substances, preserving agents, vitamins, gelling agents, fragrances, surfactants, water, antioxidants, fillers, moisturizers or screening agents.

6. The topical composition of claim 5, wherein said fatty substance comprises an oil, wax, silicone, fatty alcohol or fatty acid.

7. The topical composition of claim 1, wherein said one or more polyols are selected from the group consisting of linear-, branched- and cyclic-saturated or unsaturated polyhydroxylated compounds having from 2 to 12 carbon atoms, and polyethers of said polyhydroxylated compounds.

8. The topical composition of claim 1, wherein said oil comprises mineral oil, liquid petroleum or jojoba oil.

9. The topical composition of claim 7, which comprises in % by weight:

| L-2-oxothiazolidine-4-carboxylic acid | 5 |
|---|---|
| Jojoba oil | 13 |
| Sipol wax | 6 |
| Isopropyl palmitate | 2 |
| Glycerol | 15 |
| Alkyl paraben | 0.5 |
| Fragrance | 1 |
| Water | 100. |

10. The topical composition of claim 1, wherein said polyol is selected from the group consisting of glycerol, sorbitol, ethylene glycol, propylene glycol, butylene glycol, hexylene glycol, pentylene glycol, butylidiglycol, 1,2,3-trihydroxyhexane, dipropylene glycol and hexaglycerol.

11. The topical composition of claim 1, wherein the ratio $(I)/(II) \leq 1/4$.

12. The topical composition of claim 1, which further comprises water.

13. The topical composition according to claim 12, wherein the amount of water is less than or equal to 35% by weight relative to the total weight of the composition.

14. The topical composition of claim 12, which is suitable for the depigmentation or bleaching of human skin or of human hair.

15. The topical composition of claim 12, which is suitable for prevention of hair loss or to stimulate the regrowth of the hair.

16. The topical composition of claim 12, wherein the aqueous phase is neutralized by adjusting its pH to a value between about 6 and 8.

17. A method of depigmenting or bleaching mammalian skin or both, which comprises administering to the skin of a mammal in need of depigmenting or bleaching or both an effective amount of a composition which comprises an amount of L-2-oxothiazolidine-4-carboxylic acid (I), and at least one polyol (II), the amount by weight of compounds (I) and (II) being in the relationship: $(I)/(II) \leq 1/3$.

18. The method of claim 17, wherein said L-2-oxothiazolidine-4-carboxylic acid is in a cosmetic composition comprising from about 0.1 to 10% by weight based upon the total weight of the composition.

19. The method of claim 17, wherein said mammal is a human.

20. The method of claim 18, wherein said L-2-oxothiazolidine-4-carboxylic acid is present in an amount of from about 2 to 5% by weight.

21. The method of claim 17, wherein said composition is topically administered.

22. The method of claim 17, wherein said composition is aerosolically administered.

23. The method of claim 17, wherein said polyol of said composition is selected from the group consisting of glycerol, sorbitol, ethylene glycol, propylene glycol, butylene glycol, pentylene glycol, hexylene glycol, butyldiglycol, 1,2,3-trihydroxyhexane, dipropylene glycol and hexaglycerol.

* * * * *

UNITED STATES PATENT AND TRADEMARK OFFICE
CERTIFICATE OF CORRECTION

PATENT NO. : 6,063,389

DATED : May 16, 2000

INVENTOR(S): Véronique CHEVALIER, et al.

It is certified that an error appears in the above-identified patent and that said Letters Patent is hereby corrected as shown below:

Column 3, line 51, "Peferably" should read --Preferably--.

Signed and Sealed this

Twenty-fourth Day of April, 2001

Attest:

NICHOLAS P. GODICI

Attesting Officer

Acting Director of the United States Patent and Trademark Office